US008083748B2

(12) United States Patent
Schaeffer

(10) Patent No.: US 8,083,748 B2
(45) Date of Patent: Dec. 27, 2011

(54) DEVICE AND METHOD FOR MIXING AND DISPENSING A BONE CEMENT MIXTURE

(75) Inventor: Darin G. Schaeffer, Bloomington, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 1031 days.

(21) Appl. No.: 11/965,431

(22) Filed: Dec. 27, 2007

(65) Prior Publication Data

US 2009/0171362 A1    Jul. 2, 2009

(51) Int. Cl.
*A61B 17/58* (2006.01)
*A61B 17/60* (2006.01)
*A61F 2/00* (2006.01)

(52) U.S. Cl. ............................ 606/94; 606/279; 606/105

(58) Field of Classification Search .............. 606/92–94; 604/191, 89, 91; 222/137, 145.5, 145.6, 222/327, 387

See application file for complete search history.

(56) References Cited

U.S. PATENT DOCUMENTS

| | | |
|---|---|---|
| 3,212,685 A | 10/1965 | Swan et al. |
| 3,223,083 A | 12/1965 | Cobey |
| 4,312,343 A | 1/1982 | Leveen et al. |
| 1,940,459 A | 7/1990 | Noce et al. |
| 5,226,877 A | 7/1993 | Epstein |
| 5,468,245 A | 11/1995 | Vargas, III |
| 5,927,562 A | 7/1999 | Hammen et al. |
| 6,676,664 B1 | 1/2004 | Al-Assir |
| 7,018,382 B2 | 3/2006 | Merboth et al. |
| 7,135,027 B2 | 11/2006 | Delmotte |
| 2002/0016603 A1 | 2/2002 | Wells |
| 2002/0032447 A1 | 3/2002 | Weikel et al. |

FOREIGN PATENT DOCUMENTS

| | | |
|---|---|---|
| DE | 37 04 453 A1 | 8/1988 |
| EP | 0 217 546 A1 | 4/1987 |
| EP | 0 733 378 A2 | 9/1996 |
| EP | 0 919 206 A | 6/1999 |
| GB | 2 133 288 A | 7/1984 |
| GB | 2 139 708 A | 11/1984 |
| WO | WO 95/22941 | 8/1995 |
| WO | WO 01/93787 A | 12/2001 |
| WO | WO 2004/002375 | 1/2004 |
| WO | WO 2005/097239 A1 | 10/2005 |
| WO | WO 2006/124634 A1 * | 11/2006 |

* cited by examiner

*Primary Examiner* — Thomas C. Barrett
*Assistant Examiner* — Andrew Yang
(74) *Attorney, Agent, or Firm* — Woodard, Emhardt, Moriarty, McNett & Henry LLP

(57) ABSTRACT

In at least one embodiment of the present invention, a device for mixing and dispensing a bone cement mixture is provided. The device comprises a first chamber and a second chamber. The first chamber is for containing a first bone cement component. The second chamber is for containing a second bone cement component. A valve is in fluid communication with the first and second chambers. A first and a second plunger are respectively within the first and second chambers and are configured to actuate within their respective chambers. When the valve is in a first position actuating the first plunger advances the first bone cement component into the second chamber to form the bone cement mixture.

19 Claims, 4 Drawing Sheets

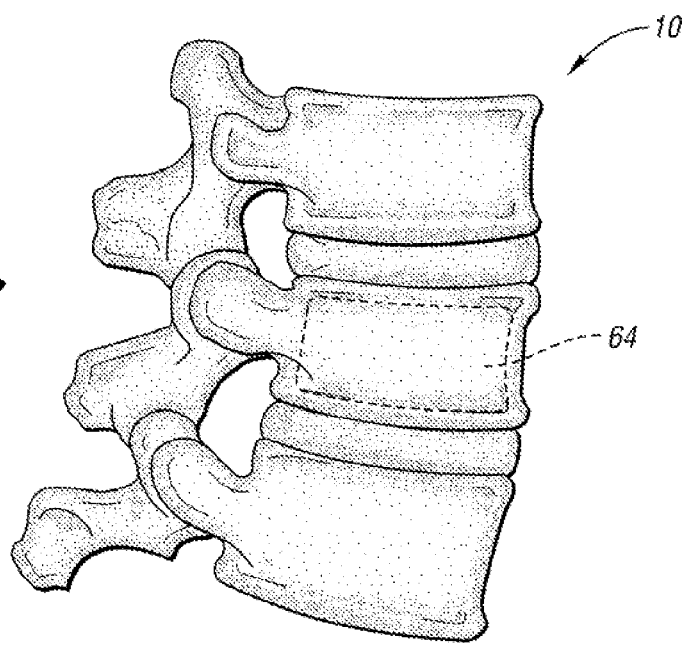
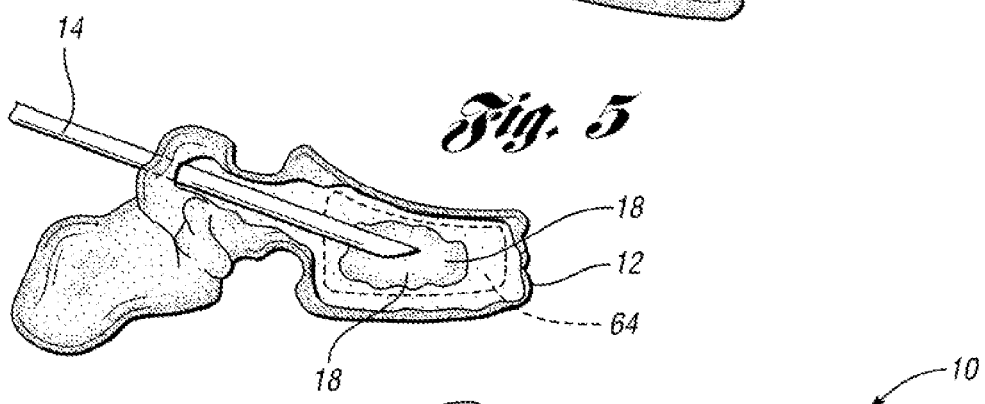
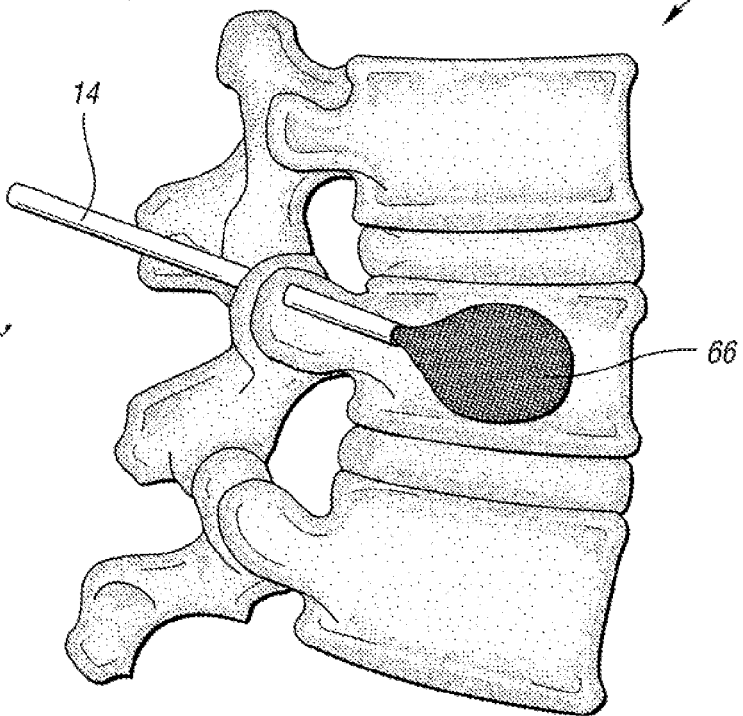

DEVICE AND METHOD FOR MIXING AND DISPENSING A BONE CEMENT MIXTURE

BACKGROUND OF THE INVENTION

1. Field of the Invention

The present invention relates to a device, a kit and a method for mixing and dispensing a bone cement mixture.

2. Background

There is a clinical need to fill and stabilize damaged bones of patients, such as for example, filling defects in collapsed vertebra of patients suffering from severe back pain caused by osteoporosis, metastatic tumors or back injuries. Currently, these defects are repaired using multi-component bone cements that are mixed in open containers, transferred to a device and injected into the damaged bone where the mixture chemically reacts or cures to form a solid support structure.

The most widely used bone cements are based on polymethylmethacrylate (PMMA) and hydroxyapatite. These materials have relatively good strength characteristics, but have a number of drawbacks. These cements are a two-part chemically reactive system and have approximately five to ten minutes of working time once the components are mixed. As for example with the PMMA based system, one of the components is a liquid monomer methylmethacrylate (MMA), which is noxious and toxic to handle. The other component, the polymer component PMMA, is a powder that can be difficult to mix thoroughly. Moreover, current methods of mixing these two components together are typically done by hand in an open container or dish. This procedure permits significant vaporization of the noxious liquid monomer MMA. Also, the working time increases between mixing and dispensing because once the mixture is mixed it then needs to be transferred to a syringe for injection into the damaged bone. Moreover, the working time is limited because the viscosity of the cement constantly increases during mixing, thus making transferring of the mixture to the syringe and injection of the mixture into the damaged bone more difficult. Often, very high injection pressures and/or large bore needles may be necessary to inject the mixture, especially if it's near the end of the cements working time.

BRIEF SUMMARY OF THE INVENTION

Embodiments of the present invention provide a device, a kit and a method that facilitates mixing and dispensing of the bone cement mixture such that the interventionalist and the patient have minimal exposure to the noxious vapors of the monomer as well as providing more flexible working times for suitable injection-ability of the mixture into the damaged bone.

In at least one embodiment of the present invention, a device for mixing and dispensing a bone cement mixture is provided. The device comprises a first chamber and a second chamber. Each chamber has a proximal end and a distal end. The first chamber is configured for containing a first bone cement component and the second chamber is configured for containing a second bone cement component. A first plunger and a second plunger are disposed cooperatively within the first and second chambers, respectively, and configured to actuate within the corresponding chamber. In fluid communication with the first and second chambers is a valve proximate the distal ends of the first and second chambers. The valve includes a first position configured to cooperate with the first plunger during actuation of the first plunger to advance the first bone cement component from the first chamber into the second chamber. Within the second chamber, the first bone cement component mixes with the second bone cement component to form the bone cement mixture. An outlet is in fluid communication with the valve for dispensing the bone cement mixture from the device.

In at least one other embodiment of the present invention, a bone cement substitute kit for mixing a bone cement mixture and dispensing the bone cement mixture into a damaged bone of a patient is provided. The kit comprises a first bone cement component and a second bone cement component. A device includes a first chamber and a second chamber. Each chamber has a proximal end and a distal end. The first chamber is configured for containing the first bone cement component and the second chamber is configured for containing the second bone cement component. A first plunger and a second plunger are disposed cooperatively within the first and second chambers, respectively, and configured to actuate within the corresponding chamber. In fluid communication with the first and second chambers is a valve proximate the distal ends of the first and second chambers. The valve includes a first position configured to cooperate with the first plunger during actuation of the first plunger to advance the first bone cement component from the first chamber into the second chamber. Within the second chamber, the first bone cement component mixes with the second bone cement component to form the bone cement mixture. An outlet is in fluid communication with the valve for dispensing the bone cement mixture from the device. In fluid communication with the outlet is a needle configured for receiving the bone cement mixture from the device and for advancing the bone cement mixture into the damaged bone of the patient.

In at least one other embodiment of the present invention, a method for mixing a bone cement mixture and for dispensing the bone cement mixture into a damaged bone of a patient is provided. The method comprises providing a device including a first chamber and a second chamber. Both the first and second chambers have a proximal end and a distal end. A valve located proximate the distal ends of the first and second chambers is in fluid communication with the first and second chambers. A first plunger and a second plunger are disposed cooperatively within the first and second chambers, respectively, and are configured to actuate within their corresponding chamber. The first bone cement component is introduced into the first chamber. The second bone cement component is introduced into the second chamber. The first bone cement component is mixed with the second bone cement component which includes positioning the valve in a first position and actuating the first plunger to advance the first bone cement component into the second chamber such that the first bone cement component mixes with the second bone cement component to form the bone cement mixture within the second chamber. A needle in fluid communication with the device is inserted into the damaged bone of the patient. Via the needle, the bone cement mixture is dispensed from the device into the damaged bone of the patient. The bone cement is cured to stabilize the damaged bone of the patient.

Further objects, features and advantages of the invention will become apparent from consideration of the following description and the appended claims when taken in connection with the accompanying drawings.

BRIEF DESCRIPTION OF THE DRAWINGS

FIG. 5 is a partial side view of a device for stabilizing a collapsed vertebra in accordance with yet another embodiment of the present invention;

FIG. 6 is a partial side view of a stabilized collapsed vertebra in accordance with one example of the present invention;

FIG. 7 is a partial side view of a device for stabilizing a collapsed vertebra in accordance with another embodiment of the present invention;

FIG. 8b is an exploded view of the bone cement substitute kit depicted in FIG. 8a.

DETAILED DESCRIPTION OF THE INVENTION

Details embodiments of the present invention are disclosed herein. It is understood however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis with the claims and for teaching one skilled in the art to practice of the present invention.

Examples of the present invention seek to overcome some of the concerns associated with stabilizing and/or repairing the damaged bone of a patient with a bone cement while minimizing toxic effects to both the patient and the interventionalist, and enhancing the ease of handling of the bone cement for both mixing and introduction into the damaged bone.

Employing the principles of the present invention is, for example, a device, a kit and a method for stabilizing and/or repairing a damaged bone of a patient. The device, which is utilized in both the kit and the method, is a closed mixing and dispensing system having two chambers that are in fluid communication with one another. Each chamber is initially for containing, for example, one of the components of a two component bone cement system. The device is configured such that the first bone cement component can be advanced from the first chamber into the second chamber so as to mix with the second bone cement component in the second chamber to form a bone cement mixture. The bone cement mixture, if needed, can be subsequently advanced back into the first chamber and vice versa until the bone cement mixture is thoroughly mixed. The device may also be in fluid communication with a needle inserted into the damaged bone of a patient. The device is configured such that the bone cement mixture may be advanced from the device into the damaged bone of a patient via the needle. The device preferably mixes the bone cement components together without releasing noxious monomer fumes contained in one of the bone cement components. Moreover, since the device is configured to dispense the bone cement mixture there is no need for transferring the mixture from another source into the device. Accordingly, the device minimizes the mixing and dispensing time of the bone cement and thus, enhances the remaining working time for introducing the mixture into the damaged bone. Once the bone cement is introduced into the damaged bone of the patient it cures to form a solid structure which stabilizes the bone.

Figure 1:
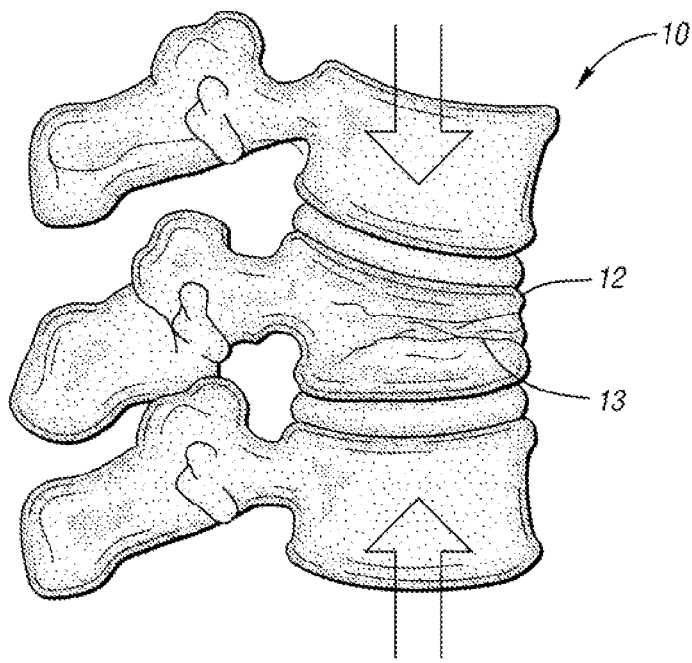
FIG. 1 is a perspective view of a collapsed vertebra.

Referring now to the drawings, FIG. 1 illustrates a vertebra 10 which includes a collapsed vertebra 12 with a compression fracture 13. The vertebra 10 may be for example in the thoracic or lower spine of the patient. In the compression fracture 13 of the vertebra 12, the bone tissue of the vertebral body collapses. This condition is commonly caused by osteoporosis and less often by a tumor, or trauma to the back.

Figure 2:
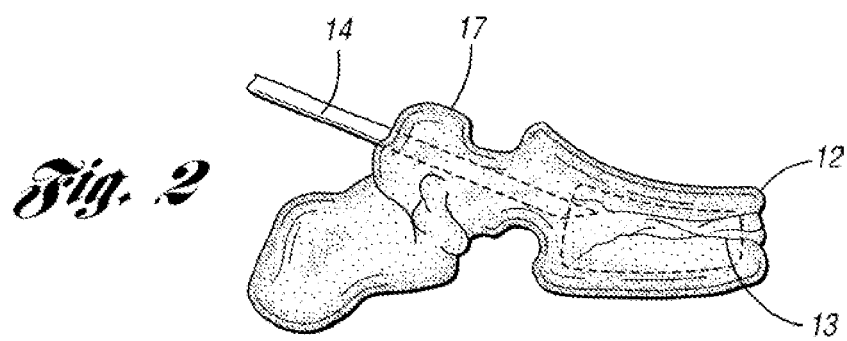
FIG. 2 is a partial side view of a device for stabilizing a collapsed vertebra in accordance with one embodiment of the present invention.
Figure 3:
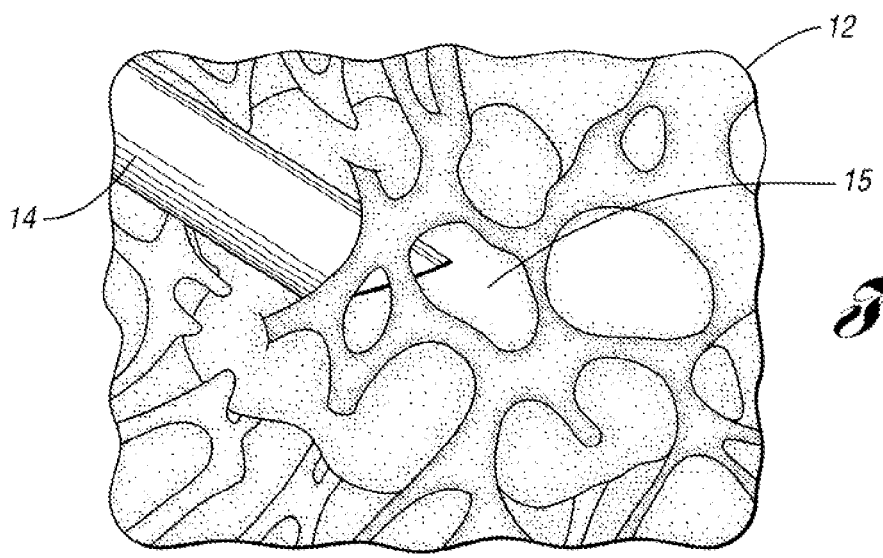
FIG. 3 is an enlarged view of FIG. 2.

Referring now to FIGS. 2 and 3, at least one embodiment of the present invention is provided. The collapsed vertebra 12 may be stabilized by either verteborplasty or kyphoplasty, both of which are medical procedures for introducing bone cement into the collapsed vertebra. These procedures stabilize the collapsed vertebra by filling in open spaces within the vertebra 12 to provide a more continuous and solid form. Kyphoplasty may further stabilize the vertebra 12 by restoring vertebral spacing which alleviates nerve pinching from the vertebra 12. It should be noted that the present invention applies to both of these medical procedures and other procedures for stabilizing and/or repairing damaged bones of patients despite many of the various embodiments discussed herein are described using verteborplasty.

Verteborplasty involves that a patient remain lying throughout the entire procedure. It is performed under a local anesthesia and/or a light sedative. A small nick is then made in the skin near the spine and a needle 14 is inserted percutaneously. As illustrated in FIG. 3, the needle 14 may be inserted into the interior 15 of the vertebra 12, for example via or through the left or right pedicle 17 of the vertebra 12.

Referring to FIGS. 5 and 6, the bone cement mixture 18 may be dispensed from a device (not shown) through the needle 14 and into the vertebra 12 to form a solid structure 64 that supports the collapsed vertebra 12. The bone cement mixture 18 forms the solid structure 64 by chemically reacting or curing to become a solid. The stabilizing structure 64 may be formed within and/or about the collapsed vertebra 12 and may help restore vertebral spacing and alleviate nerve pinching by supporting the collapsed vertebra 12 generally in at least a compressive mode. Preferably, the structure substantially fills in the open spaces 15 of the collapsed vertebra 12 providing a more dense and continuous vertebra 12 which enhances mobility of the patient.

Figure 4:
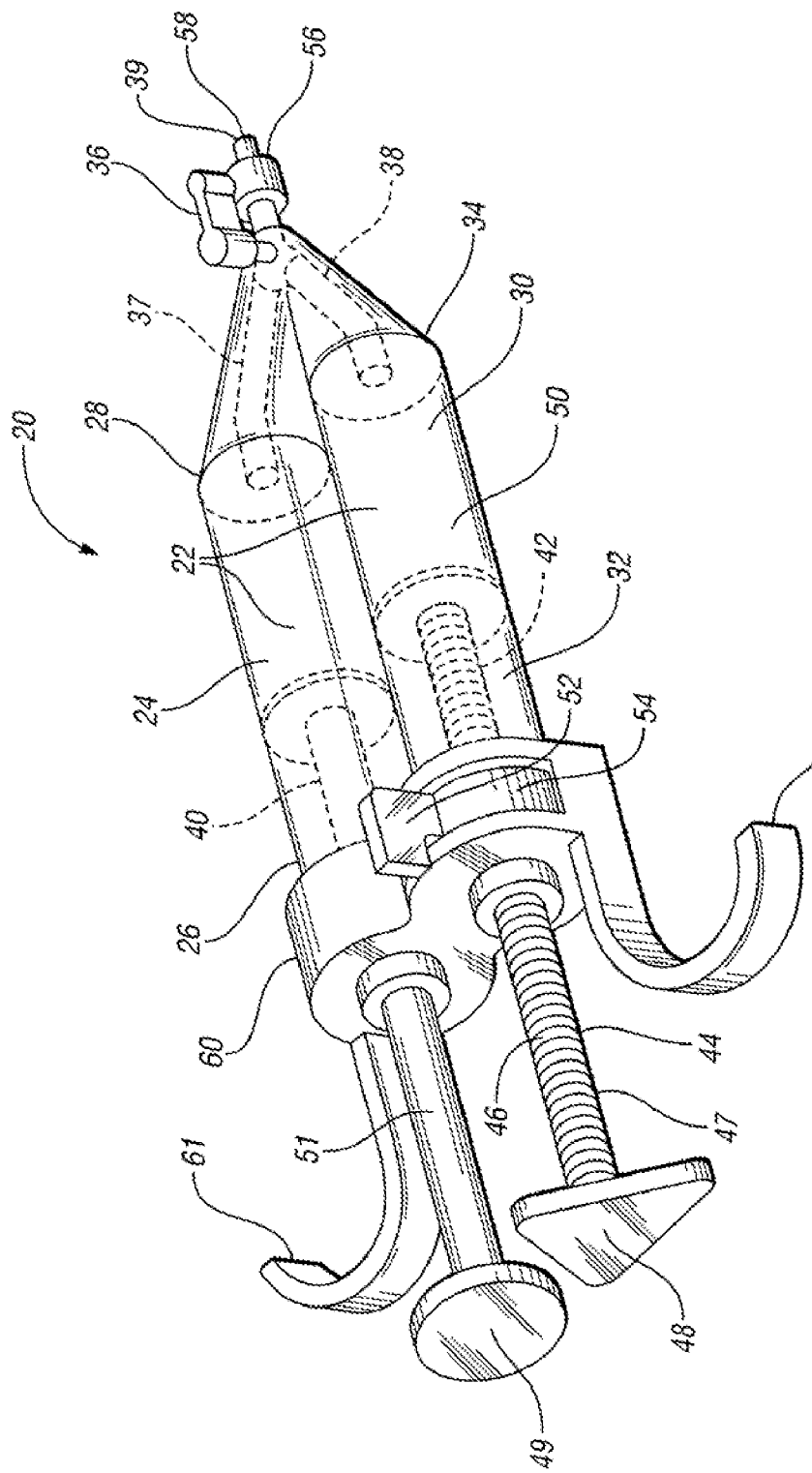
FIG. 4 is a perspective view of a device for stabilizing a collapsed vertebra in accordance with another embodiment of the present invention.

Referring to FIG. 4, at least one embodiment of a device for mixing a bone cement mixture and for dispensing the mixture is provided. The device 20 or novel syringe comprises a body 22 that includes a first chamber 24 and a second chamber 30. The first chamber 24 has a proximal end 26 and a distal end 28. The second chamber 30 also has a proximal end 32 and a distal end 34. The two chambers 24 and 30 are preferably juxtaposed such that their distal ends 28 and 34 and the proximal ends 26 and 32 are correspondingly positioned adjacent one another.

The first chamber 24 is initially for containing a first bone cement component and the second chamber 30 is initially for containing a second bone cement component. For example, a bone cement system may be comprised of separate components A and B. These components may be a liquid and/or a solid, which when mixed together chemically react to form a solid structure. Component A may be initially contained in the first chamber 24 and component B may be initially contained in the second chamber 30 or vice versa.

To further illustrate, component A, for example, is liquid monomer MMA with a relatively low viscosity of about 0.6 centipoise at room temperature and component B is solid polymer powder of PMMA. When the MMA is mixed with the PMMA, a chemically reacting paste may be formed which continually increases in viscosity over a working time of about 5 to 10 minutes to form a solid structure. In another example, component A may be sodium phosphate and component B may be solid powder of monocalcium phosphate, tricalcium phosphate, calcium carbonate or mixtures thereof that form a chemically reacting solution when mixed with sodium phosphate, which also increases in viscosity over a working time of about 5 to 10 minutes to form a solid structure.

A valve 36 may be located proximate the distal ends 28 and 34 of the first and second chambers. The valve 36 is in fluid communication with the first and second chambers 24 and 30. In one example, the body 22 further includes conduits 37 and 38 coupling the first and second chambers 24 and 30, respectively with the valve 36. The valve 36 is configured for dispensing the bone cement mixture from the device 20 via outlet 39. In fluid communication with conduits 37 and 38, outlet 39 allows the bone cement mixture to be dispensed therethrough towards the patient. In one example, the valve 36 may be a three way valve selectively providing fluid communication between both chambers 24 and 30 as well as providing exit of the cement mixture through the outlet 39 for dispensing from either of the chambers 24 and 30. Moreover, the valve 36 may also provide an inlet for receiving either or both of the bone cement components into their respective chambers 24 and 30.

The device 20 further comprises a first plunger 40 disposed within the first chamber 24 and configured to actuate within the chamber 24. The device 20 further comprises a second plunger 42 that is disposed within the second chamber 30 and configured to actuate within the second chamber 30. For example, the plungers 40 and 42 may actuate by sliding towards the distal ends 28 and 34 of their respective chambers 24 and 30. Moreover, in one example, either or both plungers may be free to slide towards the proximal ends 26 and 32 in response to an increase in pressure within their respective chamber 24 and 30. This may be due, for example, from monomer vapor pressure build-up within the respective chamber or a bone cement component or mixture being advanced from the other chamber into the respective chamber.

In at least one embodiment, one of the first and second plungers 40 and 42 is a screw-gear plunger 44, shown in this example as the second plunger 42. The screw-gear plunger 44 includes grooves 46 formed on a shaft 47 of the plunger 44 and a handle 48 disposed at the proximal end of the shaft 47.

The screw-gear plunger 44 has a corresponding chamber, shown in this example as the second chamber 30, which is a high pressure injection chamber 50. The high pressure chamber 50 is adapted for withstanding positive displacement pressures associated with advancing "paste like" fluids through the conduit 38 and valve 36. In one example, the viscosity of the "paste like" fluid is greater than about 1,000 centipoise. The high pressure chamber may be made of glass or other suitable materials known in the art for high pressure devices.

In this embodiment, the high pressure injection chamber 50 includes a locking device 52 which includes a cam 54. The locking device 52 may be disposed about the plunger shaft 47 and disposed at the proximal end 32 of the chamber 50. When the locking device 52 is in a locked position, the cam 54 engages the grooves 46 and the screw-gear plunger 44 is actuated by turning the handle 48 where the cam 54 and the grooves 46 cooperate to advance the screw gear plunger 44 towards the distal end 34 of the high pressure chamber 50. When the locking device 52 is in an unlocked position, the cam 54 is disengaged or spaced apart from the grooves 46 and the screw-gear plunger 44 is actuated by pushing the handle 48 of the screw-gear plunger 44 towards the distal end 34 of the high pressure injection chamber 50.

The valve 36 preferably has at least a first position and a second position. In one example, when the valve 36 is in the first position, actuating the first plunger 40 advances the first bone cement component from the first chamber 24 into the second chamber 30 such that the first bone cement component mixes with the second bone cement component to form the bone cement mixture within the second chamber 30. With the valve 36 still in the first position, the second plunger 42 may then be actuated to advance the bone cement mixture from the second chamber 30 into the first chamber 24. This process of advancing the bone cement mixture between the chambers 24 and 30 may be repeated until the bone cement components are thoroughly mixed together to the satisfaction of the interventionalist.

When the valve 36 is in a second position, actuating one of the first and second plungers 40 and 42 dispenses the bone cement mixture from the device 20 by advancing the mixture from the corresponding chamber 24 and 30 through the valve 36 and the outlet 39. In at least one embodiment, the plunger that is used to dispense the cement mixture from the device 20 is the screw-gear plunger 44. In this example, the locking device 52 is in a locked position such that the cam 54 engages the grooves 46 on the shaft 47. The handle 48 is turned by the interventionalist and the screw-gear plunger 44 advances the bone cement mixture from the high pressure injection chamber 50 through the valve 36 thereby dispensing the mixture from the device 20. Alternatively, the other plunger 40 may be actuated by pushing the plunger towards the distal end 28 of the first chamber 24 to dispense the bone cement mixture from the first chamber 24. This procedure may be used when the bone cement mixture has a relatively low viscosity. Whereas, the screw-gear plunger 44 may preferably be used to dispense the bone cement mixture when the viscosity of the mixture is relatively high.

The device 20 may further include as part of the valve 36, a Lure fitting nozzle 56. The bone cement mixture may be dispensed from the outlet 39 of the device 20 through the Lure fitting nozzle 56. The Lure fitting nozzle 56 typically has a tapered end 58 that facilitates connecting to various types of cannula, tubing, needles or other similar medical devices.

In at least one embodiment, the device 20 further comprises an end cap 60 disposed at the proximal ends 26 and 32 of the first and second chambers 24 and 30 that forms a closure for both chambers 24 and 30. The end cap 60 may also include the locking device 52. The end cap 60 provides an interface for positioning each of the plungers 40 and 42, preferably concentrically, within the corresponding chambers 24 and 30. Moreover the end cap 60 may also include two hook shaped handles 61 and 62 which are disposed at opposite ends of the end cap 60 which are for gripping the device 20 by an interventionalist.

In at least one embodiment, the handle 48 of the screw-gear plunger 44 is positioned along the shaft 47 and disposed outside of the high pressure chamber 50 and has, for example, a triangular shape for facilitating turning of the screw-gear plunger 44. Alternatively, the other plunger 40 may have a handle 49 positioned along a shaft 51 which is disposed outside the corresponding chamber 24 that has, for example, a flat disk shape to facilitate pushing of the plunger 40 towards the distal end 28.

Referring to FIG. 7, at least one other embodiment for stabilizing a collapsed vertebra 12 of a patient is provided. The method includes placing a balloon 66 into the collapsed vertebra 12. The balloon 66 may be positioned in the vertebra 12 for example via the needle 14, a catheter or mandrel. The balloon 22 is then filled with the bone cement mixture and sealed. The balloon 66 may be sealed for example by twisting the needle 14 and shearing the corresponding end portion of the balloon 66 or alternatively by applying any suitable adhesive, such as a cyanoacrylate, to the end portion. The cement mixture within the sealed balloon 66 cures to form a solid support structure 64 within the collapsed vertebra 12.

The balloon 66 may be made of any suitable material used for medical intracorporeal balloon devices. However, a polymer impermeable to body fluids and MMA may be preferred. An example of such material is polyethylene terephthalate (PET) or polybutylene terephthalate (PBT).

The interventionalist may also assess whether the collapsed vertebra 12 is sufficiently filled via fluoroscopy. If the collapsed vertebra 12 is not sufficiently filled, an additional balloon may be placed within the collapsed vertebra 12 and the filling, solidifying and/or curing and sealing steps may be repeated.

Figure 8A:
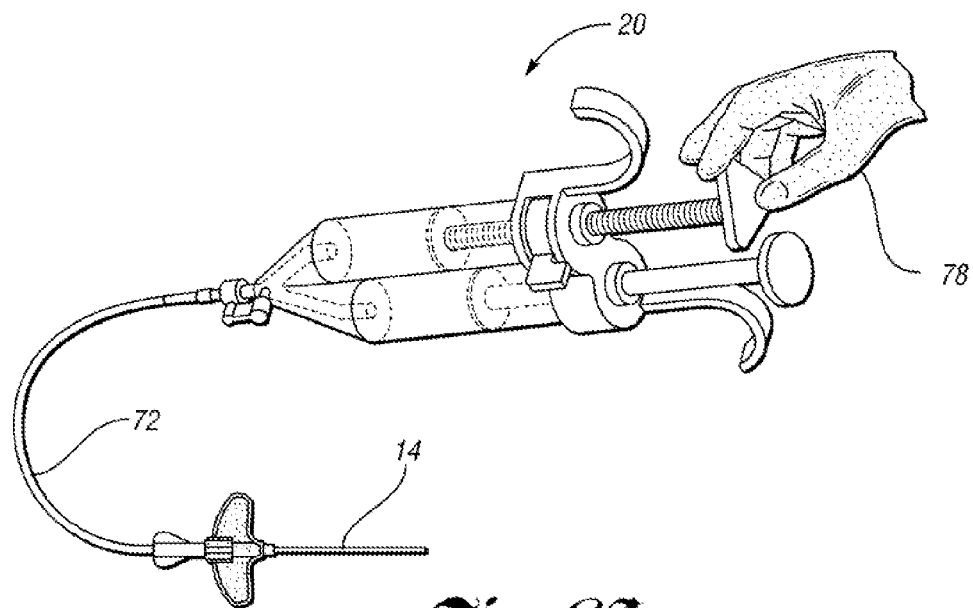
FIG. 8a is a side view of a bone cement substitute kit in accordance with one embodiment of the present invention.
Figure 8B:
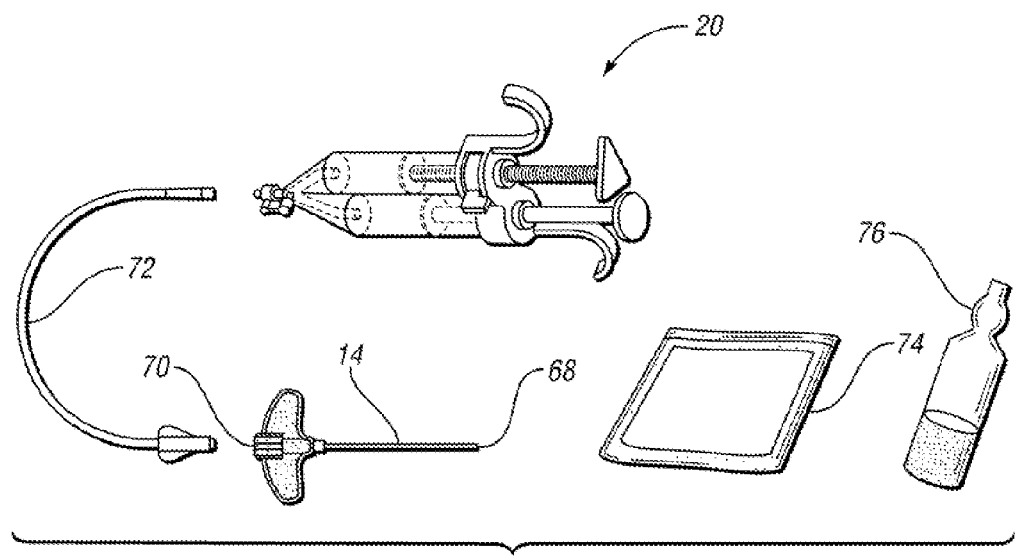

Referring also to FIGS. 8a and 8b, at least one embodiment of a bone cement substitute kit is provided. The kit includes a device 20 as discussed in the forgoing paragraphs as well as the needle 14 which is configured for fluid communication with the device 20 and for advancing the bone cement mixture into the collapsed vertebra 12. The needle 14 may have a beveled edge end 68 for easy insertion and removal from the collapsed vertebra 12. The other end 70 of the needle 14 may be directly coupled to the device 20 or indirectly coupled via tubing 72. The tubing 72 provides fluid communication between the device 20 and the needle 14. Preferably, the tubing 72 may be flexible to facilitate maneuvering of the device 20 during injection of the bone cement into the damaged bone.

The kit may further comprise a sealed envelope 74 containing a component of the bone cement, such as PMMA, and sealed container 76 containing the other component of the bone cement, such as MMA. Alternatively, either or both the first and second components of the bone cement may already be contained within the first and second chambers 24 and 30 of the device 20 as packaged.

In at least one embodiment, the device 20 includes a third position for the valve 36, which closes off fluid communication between both chambers 24 and 30 and between the chambers 24 and 30 and the outlet 39. The third position of the valve 39 may facilitate packaging and handling of the kit when the bone cement components are pre-packaged within their respective chambers 24 and 30. Additionally, the kit may further include a balloon 66 (shown in FIG. 7) for receiving the bone cement mixture 18.

As a person skilled in the art will readily appreciate, the above description is meant as an illustration of the implementation of the principles of this invention. This description is not intended to limit the scope or application of this invention in that the invention is susceptible to modification variation and change, without departing from the spirit of this invention, as defined in the following claims.

The invention claimed is:

1. A device for mixing and dispensing a bone cement mixture, the device comprising:
a first chamber and a second chamber each having a proximal end and a distal end, the first and second chambers being configured to contain respectively a first bone cement component and a second bone cement component;
a first plunger and a second plunger disposed cooperatively within the first and second chambers, respectively, and configured to actuate within the corresponding chamber;
a valve proximate the distal ends of the first and second chambers and being in fluid communication with the first and second chambers, the valve including a first position being configured to cooperate with the first plunger during actuation of the first plunger to advance the first bone cement component from the first chamber into the second chamber such that the first bone cement component mixes with the second bone cement component to form the bone cement mixture within the second chamber; and
an outlet in fluid communication with the valve for dispensing the bone cement mixture from the device,
wherein one of the first and second plungers is a screw-gear plunger including grooves and a handle and wherein the corresponding chamber is a high pressure injection chamber including a locking device having locked and unlocked positions, the locking device including a cam configured to engage the grooves in the locked position, the screw-gear plunger being actuated by turning the handle, cooperating the cam and the grooves to advance the screw-gear plunger towards the distal end of the high pressure chamber, the cam configured to disengage from the grooves in the unlocked position, the screw-gear plunger being actuated by pushing the screw-gear plunger towards the distal end of the high pressure injection chamber.

2. The device according to claim 1 wherein the valve in the first position is configured to cooperate with the second plunger during actuation of the second plunger to advance the bone cement mixture from the second chamber into the first chamber.

3. The device according to claim 1 wherein the valve includes a second position being configured to cooperate with one of the first and second plungers during actuation of the one of the first and second plungers to dispense the bone cement mixture from the device.

4. The device according to claim 1 wherein the one of the first and second plungers is configured to be actuated by pushing the plunger towards the distal end of the corresponding chamber.

5. The device according to claim 1 wherein the screw-gear plunger is configured to dispense the bone cement mixture from the high pressure injection chamber by turning the handle when the locking device is in the locked position.

6. The device according to claim 1 wherein the first and second chambers are juxtaposed and include an end cap proximate the proximal ends of the first and second chambers, the end cap including the locking device and providing an interface for positioning each of the plungers within the corresponding chamber.

7. A bone cement substitute kit for mixing a bone cement mixture and dispensing the bone cement mixture into a damaged bone of a patient, the kit comprising:
a first bone cement component and a second bone cement component; a device including:
a first chamber and a second chamber each having a proximal end and a distal end, the first and second chambers being configured to contain respectively the first and second bone cement components;
a first plunger and a second plunger disposed cooperatively within the first and second chambers, respectively, and configured to actuate within the corresponding chamber;
a valve proximate the distal ends of the first and second chambers and being in fluid communication with the first and second chambers, the valve including a first position being configured to cooperate with the first plunger during actuation of the first plunger to advance the first bone cement component from the first chamber into the second chamber such that the first bone cement component mixes with the second bone cement component to form the bone cement mixture within the second chamber; and an outlet in fluid communication with the valve for dispensing the bone cement mixture from the device; and a needle in fluid communication with the outlet and configured for receiving the bone cement mixture from the device and for advancing the bone cement mixture into the damaged bone of the patient.

8. The kit according to claim 7 wherein the valve in the first position is configured to cooperate with the second plunger during actuation of the second plunger to advance the bone cement mixture from the second chamber into the first chamber.

9. The kit according to claim 7 wherein the valve includes a second position being configured to cooperate with one of the first and second plungers during actuation of the one of the first and second plungers to dispense the bone cement mixture from the device.

10. The kit according to claim 9 wherein the valve includes a third position that closes off fluid communication between the first and second chambers and the outlet, and wherein the kit is packaged such that the valve is in the third position and the first and second bone cement components are contained respectively within the first and second chambers.

11. The kit according to claim 7 further comprising a tubing configured to couple to both the device and the needle and to provide fluid communication between the device and the needle.

12. The kit according to claim 7 wherein one of the first and second plungers is a screw-gear plunger including grooves and a handle and wherein the corresponding chamber is a high pressure injection chamber including a locking device having locked and unlocked positions, the locking device including a cam configured to engage the grooves in the locked position, the screw-gear plunger being actuated by turning the handle, cooperating the cam and the grooves to advance the screw-gear plunger towards the distal end of the high pressure chamber, the cam configured to disengage from the grooves in the unlocked position, the screw-gear plunger being actuated by pushing the screw-gear plunger towards the distal end of the high pressure injection chamber and wherein the one of the first and second plungers is configured to be actuated by pushing the plunger towards the distal end of the corresponding chamber.

13. The kit according to claim 12 wherein the screw-gear plunger is configured to dispense the bone cement mixture from the high pressure injection chamber by turning the handle when the locking device is in the locked position.

14. The kit according to claim 7 further comprising a balloon configured for positioning within the damaged bone of the patient and for receiving the bone cement mixture from the needle.

15. A method for mixing a bone cement mixture and dispensing the bone cement mixture into a damaged bone of a patient, the method comprising:

providing a device including a first chamber and a second chamber each having a proximal end and a distal end, a valve proximate the distal ends of the first and second chambers and in fluid communication with the first and second chambers, and a first plunger and a second plunger disposed cooperatively within the first and second chambers, respectively, and configured to actuate within the corresponding chambers;

introducing the first bone cement component and the second bone cement component respectively into the first and second chambers;

mixing the first bone cement component with the second bone cement component including:

positioning the valve in a first position; and actuating the first plunger to advance the first bone cement component into the second chamber such that the first bone cement component mixes with the second bone cement component to form the bone cement mixture within the second chamber;

inserting a needle into the damaged bone of the patient, the needle being in fluid communication with the device;

dispensing the bone cement mixture from the device into the damaged bone of the patient via the needle; and curing the bone cement mixture to stabilize the damaged bone of the patient.

16. The method according to claim 15 further comprising positioning a balloon within the damaged bone of the patient and the step of dispensing the bone cement mixture includes receiving the bone cement mixture into the balloon via the needle.

17. The method according to claim 15 wherein the step of mixing the first bone cement component with the second bone cement component further includes actuating the second plunger to advance the bone cement mixture from the second chamber into the first chamber.

18. The method according to claim 15 wherein the step of dispensing the bone cement mixture from the device includes positioning the valve in a second position and actuating one of the first and second plungers to advance the bone cement mixture from the corresponding chamber into the needle.

19. The method according to claim 15 wherein one of the first and second plungers is a screw-gear plunger including grooves and a handle and the corresponding chamber is a high pressure injection chamber including a locking device having locked and unlocked positions, the locking device including a cam, configured to engage the grooves in the locked position, wherein the step of dispensing the bone cement includes positioning the locking device into a locked position, turning a handle of the screw-gear plunger where the cam and the grooves cooperate to advance the screw-gear plunger towards the distal end of the high pressure chamber causing the bone cement to advance from the high pressure chamber into the needle.

* * * * *

UNITED STATES PATENT AND TRADEMARK OFFICE
CERTIFICATE OF CORRECTION

Page 1 of 1

PATENT NO.        : 8,083,748 B2
APPLICATION NO.   : 11/965431
DATED             : December 27, 2011
INVENTOR(S)       : Darin G. Schaeffer It is certified that error appears in the above-identified patent and that said Letters Patent is hereby corrected as shown below:

On the Title Page: please change item (73) Assignee: to read -- Cook Medical Technologies LLC, Bloomington, IN (US) --

Signed and Sealed this
Twenty-fifth Day of December, 2012

David J. Kappos
*Director of the United States Patent and Trademark Office*